United States Patent [19]

Fudenberg et al.

[11] Patent Number: 4,728,605

[45] Date of Patent: Mar. 1, 1988

[54] METHODS FOR RECOGNIZING AND DIAGNOSING SUBSETS OF ALZHEIMER'S DISEASE ASSOCIATED WITH IMMUNE SYSTEM DYSFUNCTION, AND FOR THE IN VITRO TESTING OF POSSIBLE THERAPEUTIC AGENTS FOR TREATMENT OF SAME

[76] Inventors: Herman H. Fudenberg, P.O. Box 702, Sullivan Island, S.C. 29482; Harrell D. Whitten, 2037 Lake Shore Dr., Charleston, S.C. 29412; Nemat Khansari, 1721 Ashley Hall Rd., Charleston, S.C. 29407

[21] Appl. No.: 636,287

[22] Filed: Jul. 31, 1984

[51] Int. Cl.[4] ............................................. C12Q 1/02
[52] U.S. Cl. ......................................... 435/29; 435/4; 436/501; 436/519; 436/811; 424/2; 424/3
[58] Field of Search ................. 436/59, 506, 519, 811; 435/29, 7, 4; 424/11, 2, 3

[56] References Cited

U.S. PATENT DOCUMENTS 4,196,186  4/1980  Bogoch ............................. 436/503

OTHER PUBLICATIONS

Szuchet, et al., Nature, vol. 295, (1982), pp. 66–68.
Terry, et al., Ann. Neurology, vol. 10, No. 2, (1981), pp. 184–192.
Terry, et al., Ann. Rev. Neurosci., vol. 3, (1980), pp. 77–95.
Khansari, et al., Immunobiol., vol. 164, (1983), pp. 42–50.
Isselbacher, K. J., Proc. Nat. Acad. Sci. USA, vol. 69, No. 3, (1972), pp. 585–589.
Schuller-Petrovic, et al., Nature, vol. 306, (1983), pp. 179–181.
Fontana, et al., Eur. J. Immunol., vol. 13, (1983), pp. 685–689.
Goust, et al., J. Immunol. Meth., vol. 59, (1983), pp. 29–38.
Wurtman, et al., Life Sciences, vol. 28, (1981), pp. 1091–1093.
Nybäck, et al., Psychopharmacology, vol. 61, (1979), pp. 235–238.
Cumin, et al., Psychopharmacology, vol. 78, (1982), pp. 104–111.
Abuzzahab, et al., Psychopharmacology Bull., vol. 14, No. 1, (1978), pp. 23–25.
Khansari, et al., Scand. J. Immunol., vol. 19, (1984), pp. 337–342.
Miller, et al., Clinical Immunol. Immunopath., vol. 26, (1983), pp. 446–451.
Wybran, et al., J. Immunol., vol. 123, No. 3, (1979), pp. 1068–1070.
Garson et al., Nature, vol. 298, (1982), pp. 375–377.
Fudenberg et al., Medical Hypotheses, vol. 12, (1983), pp. 85–93.
Meredith, et al., Mechanisms of Ageing and Development, vol. 9, (1979), pp. 61–77.
Perry, et al., J. Neuro. Sci., vol. 34, (1977), pp. 247–265.
Whitehouse, et al., Science, vol., 215, (1982), pp. 1237–1239.
Roberts, E., Ann. N.Y., Acad. Sci., vol., 396, (1982), pp. 165–178.

Primary Examiner—Robert J. Warden
Assistant Examiner—Stephen C. Weider
Attorney, Agent, or Firm—Iver P. Cooper

[57] ABSTRACT

A method is provided for recognizing and diagnosing diseases or conditions associated with immune system dysfunction and loss of integration of brain function, particularly a subset of Alzheimer's disease, and for the in vitro testing to determine efficacy of possible therapeutic agents. The method involves measurement of immunological parameters on peripheral blood immunocytes.

11 Claims, No Drawings

METHODS FOR RECOGNIZING AND DIAGNOSING SUBSETS OF ALZHEIMER'S DISEASE ASSOCIATED WITH IMMUNE SYSTEM DYSFUNCTION, AND FOR THE IN VITRO TESTING OF POSSIBLE THERAPEUTIC AGENTS FOR TREATMENT OF SAME

BACKGROUND OF THE INVENTION

Until recently the manifestations of cerebral senility have been thought to result from arteriosclerosis with a subsequent diminution of adequate oxygen delivery to the nervous tissue, Terry (1980). However, it is now apparent that (in at least some individuals' central nervous systems) cerebral "aging" (loss of cognitive function) is due to primary degenerative functional deficiencies in the neural cells (neurons) themselves, Whitehouse (1982). These deficiencies, when so severe as to merit being categorized separately due to the severe defect in recent memory recall and cognitive function, are termed Alzheimer's syndrome, Kateman (1976). In dementia of the Alzheimer's type, also referred to as Alzheimer's disease (AD), neuropathological brain examinations in most but not all patients have revealed some characteristic abnormalities, e.g., neuritic plaques, abnormal neurites, neurofibrillary tangles containing paired helical filaments composed of cross-linked polypeptides, that are especially prominent in the cerebral cortex and hippocampal formation, Perry (1977). In the last decade, it has been found that excessive nerve cell loss occurs in the frontal and temporal cortices of the cerebral cortex. Recently, it has been demonstrated that there seems to be a relatively specific loss (75 percent) of the neurons in the basal nucleus of Meynert, Coyle (1983). The cells affected are the major source of extrinsic cholinergic input into the cortex.

A recent article by Goldsmith, "Attempts to Vanquish Alzheimer's Disease Intensify, Take New Paths," refers to AD as a "dementing disorder for which the diagnosis is unequivocal only post-mortem, the therapy almost non-existent, and prognosis grim." JAMA 251: 1805 (Apr. 13, 1984).

Presently, AD is generally diagnosed on the basis of behavioral symptoms and psychological scoring. The diagnosis may be reinforced by morphological examination of the brain (by noninvasive methods like CAT scan) for structural abnormalities (frontal lobe cortical atrophy). In addition, biochemical examination of cerebrospinal fluid may reveal depressed levels of the enzymes choline acetyltransferase and/or acetylcholine esterase. After death, the presence of AD may be established unequivocally by the detection of atrophy of the basal nucleus of Meynert.

Research, and therapeutic efforts as well, are currently focused on efforts to facilitate the release of acetylcholine from the undegenerated neurons as well as ultimately preventing the progressive deterioration of these neurons. However, studies of more fundamental immunobiology may be more rewarding. For example, each of the major class of "immunocytes", i.e., monocytes, natural killer cells, B lymphocytes, suppressor T-cells and helper T-cells appear to have an antigenic counterpart in CNS cells, but in cells of no other organ.

EXAMPLES OF IS-CNS Antigenic Cross Reactivity (1) Oligodendrocytes share certain antigens with T suppressor cells as determined by OKT8 monoclonal antibody (Oger, et al., 1982).

(2) Purkinjie cells of many species are labeled by anti-human T-cell monoclonal antibodies (Garson, et al., 1982).

(3) Natural killer (NK) cells share antigens as defined by the anti-Leu-7 reagent with central and peripheral nervous tissue (Shuller-Petrovic, et al., 1983).

(4) Neuronal cells possess both Fc receptors and Ia antigens as do certain B lymphocytes; these two are not restricted to these two systems.

(5) Certain glial cells (astrocytes, supraependymal cells) possess Fc receptors and Ia antigens as do monocytes/macrophages; Anti-M1 (monocyte associated) monoclonal antibody stains cells within the white matter of the brain (Hauser, et al., 1983). These cells also produce interleukin-1 like molecules (Fontanal, et al. 1983).

(6) Brain synaptosome membranes possess the Thy-1 antigen (human T3) as do T helper cells.

But, the similarities between the central nervous and immune systems are striking and go far beyond this "antigen sharing". In both systems there is an intricate network in which message are transmitted to other cells not by direct contact but by soluble factors, collectively termed "neurotransmitters" and "lymphokines", respectively. We and others have found that various immunocyte subsets have receptors for endogenous neurotransmitters (acetylcholine, dopamine, serotonin, substance P) and opiate and other drugs (e.g., PCP), receptors that appear identical to those present on brain cell lines, Fudenberg (1983); Wybran (1979); Miller (1983); Bidart (1983).

Interleukins are produced by established neural cells as well as immunocytes. The neurofibrillary tangles characteristic of AD appear to be composed of substances related to amyloid, a product of abnormally functioning B-cells.

Memory is a property of both the immune and central nervous systems and is progressively impaired in Alzheimer's disease. Because of these similarities, we have previously postulated that another brain disorder, schizophrenia, is more than one disease, indeed a syndrome of diseases, Fudenberg (1983), in which deficiencies of receptor number and/or function occur. A relevant analogy is human diabetes where one type is characterized by high antibody levels against insulin receptors; another type has antibodies to the pancreatic islet cells that predominantes in a genetically predisposed (HLA-B8) group after cytomegalovirus infection; a third (non-immunologic) appears due to deficiency in numbers and/or affinity of insulin receptors.

The eventual elucidation of the pathogenesis of AD should indicate it to be a syndrome with different types of therapies necessary for the corresponding diseases. However, the number of neuronal cells (and the numbers and/or functional integrity of membrane ACh receptors) is undoubtedly a critical factor.

Unfortunately, defects in neural cell receptor number and/or function are detectable directly only upon autopsy, a rather drastic diagnostic tool. This not only hinders diagnosis and treatment, but also the simple evaluation of potential therapeutic agents.

There is a considerable demand for a therapeutic agent that can correct the impairment of cognition and subsequent steady downhill course leading to immobilization and lack of bladder and bowel sphincter function. Unfortunately, studies in the field of neuropharmacology are hampered by the fact that the molecular and neural mechanisms involved in cognitive functions are still far from being understood.

Pyrrolidone derivatives and analogs such as piracetam (1-acetamido 2-pyrrolidone) (1a,2p) and aniracetam (1-anisoyl, 2-pyrrolidone) and pramiracetam (1-pyrrolidineacetamide) have attracted interest. Piracetam has been used with mixed results for the control of the psycho-organic symptoms of old age (Nyback et al, 1979). There is some difference of opinion also as to the mechanism whereby piracetam might improve learning or memory (File and Hyde, 1979).

Wurtman, et al., 1981, suggest that piracetam might accelerate acetylcholine release by septohippocampal cholinergic neurons. Since Alzheimer's Disease is characterized by a selective loss of cholinergic neurons, they concluded that this neuronal population is involved in certain components of memory. Wurtman did not recognize, however, that AD is not a single disease but a family of related diseases requiring different therapy.

Additionally, the work of Ferris, Aging NY, 19: 475 (1982) suggested that piracetam alone was of little clinical significance in the treatment of Alzheimer-type cognitive impairment. See also Schneck, Nootropics, in Pharmacologic Investigations Into the Treatment of Alzheimer's Disease, at 362-366.

Consequently, it cannot be said that the art teaches that piracetam is effective against a particular subset of AD, indeed, there has been no recognition that different subsets exist.

Piracetam is the archetypal nootropic drug. These drugs have a selective and direct effect on the integrative brain function. Such drugs include oxiracetam, etiracetam, pramiracetam, and dipyrrolizine. The main therapeutic indications for nootropics are currently found in geriatric and organic brain syndrome, in post-traumatic and posthypoxic events, and in the learning and speech disabilities of children, though other uses are likely to be established as study of nootropics continues. Assessment of the efficacy of nootropics, either in clinical studies or in animal models is difficult. See T. M. Itil, Editorial, Nootropics: Status and Prospects, Biol. Psych. 18: 521 (1983).

Novel testing systems are critically needed to predict therapeutic effects of neuropsychotropic and nootropic agents and to monitor therapy in AD patients.

Surprisingly, we are the first to study the effect of piracetam on the immune system, even though piracetam is structurally related to polyvinylpyrrolidone (PVP), a known immune cell stimulant and B cell mitogen.

Moreover, we are the first to utilize testing of immune cells for the diagnosis and treatment of a subset of Alzheimer's Syndrome or to use such testing to evaluate in vitro a potential therapeutic agent for the treatment of an Alzheimer's Disease sufferer. Finally, we have shown that piracetam can, in this subset, correct the abnormal immunological condition now found to be characteristic of this subset of AD, in vivo and in vitro, and to reverse the integrative brain function impairment symptomatic of Alzheimer's Disease in vivo.

SUMMARY OF THE INVENTION

This invention exploits the close resemblance of the central nervous and immune systems. Specifically, diseases such as Alzheimer's Disease that are believed to be associated with defects in neural cell receptors (whether intrinsic, or secondary to immunodepression), can be diagnosed by testing of peripheral blood immunocytes. (It is, of course, impossible, prior to autopsy, to obtain an adequate number of brain cells on which to diagnose such diseases directly, but immunocytes appear to bear most, if not all, of the relevant structures). In particular, I have found that levels of interactive T cells in peripheral blood are seriously depressed in a subset of AD patients.

Moreover, this invention contemplates a method of in vitro testing of therapeutic agents for efficacy in treating the aforementioned diseases in individual patients. These agents may be tested on the appropriate peripheral blood immunocytes, which may be easily obtained. I have found that certain agents that restored interactive T cell levels in vitro also provided therapeutic benefits for the aforementioned subset of AD patients.

In addition, specific therapeutic agents for Alzheimer's Diseases, and related degenerative diseases, are disclosed herein.

One such agent is piracetam (1a;2p) which has been found to correct the immune system dysfunction typical of one Alzheimer's disease subset and to cause clinical improvement in the subset.

One object of the invention is to provide a means for diagnosing a disease of the central nervous system associated with the impairment of integrative brain function, such as those characterized by Alzheimer's syndrome, which does not require examination of difficult-to-obtain CNS cells.

Another object of the invention is to provide a means of testing other possible therapeutic agents for such diseases, again without use of difficult-to-obtain CNS cells.

Another object of the invention is to provide a therapeutic agent known to improve the immunological profile of certain Alzheimer's disease patients and believed to have the desired CNS activity.

Another object of the invention is to provide a therapeutic agent for that subset of Alzheimer's syndrome patients characterized by depressed function or level of interactive T-cells.

Another object of the invention is to provide a means of testing other possible therapeutic agents, in vitro, for use in treating that subset.

Other objects of the invention will be obvious to persons of ordinary skill in the art after consideration of the specification and claims presented.

DETAILED DESCRIPTION OF THE INVENTION

Laboratory Evaluation of New Therapeutic Agents by In Vitro Tests on Peripheral Blood Immunocytes Patients Patients consisted of 22 individuals with mild cerebral atrophy on CAT scan diagnosed as AD patients by the Global Deterioration Scale (GDS) for Assessment of Primary Degenerative Dementia (Reisberg, et al., 1982).

Controls

Controls consisted of 22 age-matched (ages 58-91) elderly healthy individuals, and 18 disease controls whose symptoms mimicked AD, but resulted from other causes (e.g., Parkinsonism, cerebrovascular accident, etc.).

Drug

Immunocytes of patients and disease controls were 1a-2p tested in vitro both with and without ($10^{-3}$–$10^{-7}$M). Oral ingestion of 1a,2p (800 mg/day) 1a-2p in tablet form (2 tablets 3 times a day) with meals, or switched to placebo after 6 months (upon deterioration, some were switched back) constituted the in vivo drug therapy.

Table 1 1 shows representative clinical values of several immunological parameters before and after 1a-2p therapy.

Therapeutic benefits from 1a-2p therapy in Interactive T cell-depressed subset of AD patients paralleled by correction of immunodepression Table 1 illustrates interactive T-cell monitoring and 1a-2p therapy in selected patients. Patients MAB, WHR, and BFP evinced interactive T-cell depression, in vitro correction by 1a-2p, and encouraging clinical improvement after in vivo administration of 1a-2p. Additionally, they showed the appropriate in vivo and in vitro changes when switched to a placebo. Patients MLH, VSB, and E.S. evinced normal interactive T-cell levels (but other immunological abnormalities), in vitro correction of said abnormalities in patients MLH and VSB, and lack of clinical improvement despite 1a-2p administration. Generally speaking, no improvement occurred in AD patients with a normal interactive T-cell level prior to 1a-2p treatment, and no change in interactive T-cell levels was seen in aged, healthy controls after administration of 1a-2p.

TABLE 1
LABORATORY VALUES AND DISEASE COURSE FROM REPRESENTATIVE INDIVIDUAL PATIENTS[a] DEMONSTRATING INTERACTIVE T-CELL MONITORING AND 1a-2p THERAPY

| Name | Stage of Disease[b] | Date | Lab abnormality Yes | Lab abnormality No | In Vitro correction by 1a-2p Yes | In Vitro correction by 1a-2p No | Given 1a-2p; if so, date |
|---|---|---|---|---|---|---|---|
| M.A.B. (1) | IV | 06/17/83 | Interactive T-cells (50% of control | | (to 100%) | | 08/21/83 |
| W.M.R. (2) | V | 09/14/83 | Interactive T-cells (48% of control | | (to 100%) | | 09/19/83 |
| B.F.P. (3) | IV | 06/28/83 | Interactive T-cells (60% of control | | (to 100%) | | 07/25/83 |
| M.L.H. (4) | IV | 06/28/83 | NK cells (20% of control) | Interactive T-cells normal | (to 100%) | Interactive T-cells normal | 07/25/83 |
| V.S.B. (5) | IV | 08/23/83 | IL-1 (40% of control) | Interactive T-cells normal | IL-1 normalized | Interactive T-cells normal | 07/25/83 |
| E.S. (6) | II | 01/25/83 | IL-2 production (40% of control) | Interactive T-cells normal | | IL-2 not corrected T-cells normal | 06/20/83 |

| Name | Correction In Vitro | Correction In Vivo Date | Correction In Vivo (Stage) | Changed to Placebo Yes | Changed to Placebo Date | Changed to Placebo No | Change In Vitro | Change In Vivo | Reinstituted on 1a-2p |
|---|---|---|---|---|---|---|---|---|---|
| M.A.B. (1) | Yes Interactive T-cells normal | 01/25/83 | Yes (II) | Yes | 02/18/84 | | Interactive T-cells dropped (60% of normal | Stage IV | Not done |
| W.M.R. (2) | Yes Interactive T-cells normal | 02/28/84 | Yes (II) | Yes | 02/13/84 | | Not done | Stage IV | Not done |
| B.F.P. (3) | Yes NK cells normal | 10/03/83 | Yes (II) | Yes | 11/07/83 | | Interactive T-cells dropped (50% of normal | Stage IV | 02/06/84 Normalize in vitro and almost in vivo (Stage I) |
| M.L.H. (4) | Yes | 11/15/83 | No change in symptoms | Yes | 11/16/83 | | | No change in symptoms | |
| V.S.B. (5) | Yes | 09/31/83 | Still (IV) | Yes | 01/03/84 | | Yes IL-1 | No change | |

TABLE 1-continued
LABORATORY VALUES AND DISEASE COURSE FROM REPRESENTATIVE INDIVIDUAL PATIENTS[a] DEMONSTRATING INTERACTIVE T-CELL MONITORING AND 1a-2p THERAPY

| | | | | | | dropped (35%; Interactive T-cells still normal | in symptoms |
|---|---|---|---|---|---|---|---|
| E.S. (6) | No correction | 08/17/83 | No correction, still (II) | Yes | 09/13/83 | No change | No change (still stage II) |

[a]Patients 1-3 show response to 1a-2p in vitro and in vivo and demonstrate importance of interactive T-cell test; patients 4-6 suggest irrelevance of in vitro correction of other tests in presence of normal interactive T-cells.
[b]V = worst; I = mild. The full scale ranges up to VII.

Measurement of Immunological Parameters

Peripheral blood lymphocytes (PBL) may be obtained by venipuncture from individuals for the desired functional immunocyte studies. Preferred protocols for a number of studies are given below.

The level of interactive T cells is depressed in that subset of AD patients who showed clinical improvement upon treatment with an agent which restored interactive T-cell levels in vitro. Immunoglobulin synthesis, IL-1 and IL-2 activity, and 2-deoxyglucose uptake were also abnormal in some AD patients, but restoration of normality by piracetam treatment was not accompanied by clinical improvement.

1. Active and total sheep erythrocyte (SRBC) rosette forming T-cells

Levels of active (active T-cells are concerned with mediator production and are a measure of the total afferent limb of cell-mediated immunity) and total T-cells may be measured, Fundenberg, Wybran and Robbins (1975). LIF production after ConA and PHA stimulation, Oppenheim and Rosenstreich (1976), were measured when indicated using methods described in Arala-Chaves, Silva, Porto, Picoto, Ramos and Fudenberg (1977).

2. Interactive T-cells

Interactive T-cells are those which bind to established human B lymphoid cell lines to form rosettes. They seem to be smaller than normal T-cells, typically 10–100 cubic microns rather than 100–200 cubic microns. These cells may be the human equivalent of mouse contrasuppressor cells. We employ the Raji B lymphoid cell line for this assay, Goust and Fudenberg (1983). The percent of rosettes formed between normal peripheral blood lymphocytes and Raji cells is 27.8±5.3 mean±S.D at a 20:1 (PBL:Raji) ratio. To perform the assay, Ficoll-Hypaque isolated PBL were suspended in RPMI-1640 medium supplemented with 1% bovine serum albumin (BSA) and adjusted to a concentration of $2 \times 10^7$ cells/ml. Raji cells were washed twice in same medium and adjusted to a concentration of $1 \times 10^6$ cells/ml. 50-ul aliquots of the two cell suspensions are then mixed (20:1 ratio of PBL to Raji), centrifuged at 150 g for 5 minutes at 4° C., and incubated for 1 hour in an ice water bath. After gentle resuspension, the percent of Raji cells surrounded by three or more lymphocytes (rosettes) were determined.

3. Natural Killer (NK) cells The Becton Dickinson HNK1 and/or LeU-11 monoclonal antibodies may be used for enumeration of natural killer cells (NK); cells from the erythroleukemic cell line K562 may be used as target cells.

Effector cells were prepared from PBL by nylon wool column separation of T- and B-cells and followed by SRBC rosette formation. Monocyte depleted, nylon wool non-adherent cells are mostly NK and K cells. 100 ul of nylon wool nonadherent cells were added with 100 ul of $^{51}$Cr-labeled target cells ($1 \times 10^4$) in the wells of a flat-bottomed microtest plate at a ratio of 50:1 or 25:1. Target cells incubated without effector cells are used to determine the level of spontaneous lysis. Maximum lysis was determined by adding 10% Triton X-100 solution (no effector cells) instead of medium to the well. The percentage cytotoxicity was calculated as:

$$\% \text{ cytotoxicity} = \frac{\text{mean cpm test} - \text{mean cpm spontaneous lysis}}{\text{mean cpm maximum lysis} - \text{mean cpm spontaneous lysis}} \times 100.$$

Each assay is performed in triplicate.

4. IL-2 activity

IL-2 activity in microculture may be measured as follows: $4 \times 10^3$ cells of a cloned IL-2 dependent T-cell line (CTLL) are washed extensively and incubated in 30 ul of supernatant in a total of 100 ul culture medium with 5% fetal calf serum at 37° C. in flat-bottomed microwells. After 24 hours, 2 uCi methyl-[$^3$H]-thymidine (2.0 ci/mmole) is added for a further 4–5 hours. Cells are then harvested onto filter paper disks using an automated cell harvester and counted in a liquid scintillation counter.

5. Immunoglobulin (IgM and IgG) synthesis

Isolated PBLs were suspended in complete RPMI at $2 \times 10^6$ cells/ml and PWM was added at a final concentration of 1:50. One half ml of the cell suspension was placed in each well of a 24-well flat bottom microtiter plate and incubated at 37° C. in a 5% $CO_2$ incubator for 8 days. For cultures containing 1a–2p, drug was added at day zero at a final concentration of $10^{-3}$M. Cultures were supplemented daily with 80 ul of nutritional cocktail as described by Mishell and Dutton (1967). The culture supernates were recovered following incubation and assayed for IgM and IgG content by the immunosorbent assay (ELISA) as described by Khansari, Fudenberg and Merler, Immunobiol 164: 12, #74 (1983).

Lymphocyte stimulation

A quantity (0.1 ml) of one tenth of one ml lymphocyte suspension ($5 \times 10^6$ cells/ml) was placed in each well of a 96-well flat bottom microtiter plate. PWM (Gibco, Grand Island Biological Co., Grand Island, NY) was added to each well at a final concentration of 1:50. A therapeutic agent, such as 1a-2p, may be added to the cells at the concentration of $10^{-3}$M and followed by incubation at 37° C. in a 5% $CO_2$ for 96 hours. The cultures were fed with 0.5 uCi of $^3$H-thymidine (New England Nuclear, Boston, MA) for additional 18 hours of incubation. After incubation, the cells were harvested and radioactivity was counted in a scintillation counter. The control cultures were treated similarly but without 1a-2p.

While specific assays for these parameters are described above, it should be understood that this invention is not limited to any specific assay method, and that no specific number of assays is required. Furthermore, this invention is not limited to the three immunological parameters listed above. Nor is it necessary that all of the aforementioned parameters be monitored in the course of testing a specific therapeutic agent or diagnosing a particular clinical condition.

This invention embraces the immunological testing of new neuropsychotropric or nootropic agents without limitation to those enumerated, and of agents having nootropic as well as other psychotropic or other drug action.

In addition to 1a-2p, other pyrrolidone derivatives and analogs, including but not limited to those listed earlier, and other B cell mitogens, are potential or recognized nootropic agents which may be tested or used therapeutically, in accordance with the teachings herein. In vitro immunological testing of pramiracetam suggests that it is a more potent nootropic agent than 1a,2p.

From the foregoing description, one skilled in the art can easily ascertain the essential characteristics of this invention and, without departing from the spirit and scope thereof, modify the invention to adapt to various usages and conditions.

The disclosures of the references cited below are incorporated by reference herein.

References

1. Whitehouse, P. J., Price, D. L., Strubb, R. G., Clark, A. W., Coule, J. T., and DeLong, M. R. Alzheimer's disease and senile dementia: Loss of neurons in the basal forebrain. Science 215, 1237, 1982.
2. Katzman, R. The prevalence and malignancy of Alzheimer's disease. Arch. Neurol. 33, 217, 1976.
3. Perry, E. K., Perry, R. H., Blessed G., and Tomlinson, E. Neurotransmitter enzyme abonormalities in senile dementia. J. Neurol. Science 34, 247, 1977.
4. Whitehouse, P. J., Price, D. L., Clarke, A. W., Coyle, J. T., and DeLong, M. R. Alzheimer's disease: evidence for selective loss of cholinergic neurons in the nucleus basalis. Ann. Neurol. 10, 122, 1981.
5. Roberts, E. Potential therapies in aging and senile dementias. Ann. NY Acad. Sci. 396, 165, 1982.
6. Meredith, P. J., and Walford, R. L. Autoimmunity, histocompatibility, and aging. Mech. Aging Dev. 9, 61, 1979.
7. Coyle, J. T., Price, D. L., and DeLong, M. R. Alzheimer's disease: a disorder of cortical cholinergic innervation. Science 219, 1184, 1983.
8. Herbert. W. Senile dementia linked to immunity gene. Science News 124, 5, 1983.
9. Longo, V. G. Behavioral and electroencephalographic effects of atropine and related compounds. Pharmacol. Rev. 18, 965, 1966.
10. Fudenberg, H. H., Whitten, H. D., Merler, E., and Farmati, O. Is schizophrenia an autoimmune receptor disorder? Med. Hypoth. 12, 85, 1983.
11. Oger, J. Szuchet, S., Antel, J., and Arnason, B. G. W. A monoclonal antibody against human T suppressor lymphocytes binds specifically to the surface of cultured oligodendrocytes. Nature 295, 66, 1982.
12. Garson, J. A., Beverley, P. C. L., Coakham, H. B., and Harper, E. I. Monoclonal antibodies against human T lymphocytes label purkinjie neurons of many species. Nature 298, 375, 1982.
13. Wybran, J., Appelboom, T., Famaeg, J. P., and Govaerts, A. Suggestive evidence for receptors for morphine and methionine-enkephalin on normal human blood T lymphocytes. J. Immunol. 123, 1068, 1979.
14. Miller, G. C., Murgo, A. J., and Plotnikoff, N. P. Enkephalines—enhancement of active T-cell rosettes from lymphoma patients. Clin. Immunol. Immunopathol. 26, 446, 1983.
15. Bidart, J. M., Motte, Ph., Assicot, M., Bohuon, C., and Bellet, D. Cathechol-O-methyl transferase activity and aminergic binding site distribution in human peripheral blood lymphocyte subpopulations. Clin. Immunol. Immunopathol. 26, 109, 1983.
16. Reisberg, B., Ferris, S. H., deLeon, M. J. and Crook, T. The Global Deterioration Scale (GDS) for assessment of primary degenerative dementia. Am. J. Psychiat. 139, 1136, 1982.
17. Fudenberg, H. H., Wybran, J. and Robbins, D. S. T-rosette-forming cells, cellular immunity and cancer (Editorial). N. Engl. J. Med. 292, 475, 1975.
18. Oppenheim, J. J. and Rosenstreich, D. L. In: In Vitro Methods in Cell Mediated and Tumor Immunity (B. R. Bloom and J. R. David, eds.). Academic Press, New York, p. 573, 1976.
19. Arala-Chaves, M. P., Silva, A., Porto, M. T., Picoto, A., Ramos, M. T. F., and Fudenberg, H. H. In vitro and in vivo studies of the target cell for dialyzable leukocyte extracts: Evidence for recipient specificity. Clin. Immunol. Immunopathol. 8, 430, 1977.
20. Goust, J. M., Chenais, F., Carnes, J. E., Hames, C. G., Fudenberg, H. H., and Hogan, E. L. Abnormal T-cell subpopulations and circulating immune complexes in the Guillain-Barre syndrome and multiple sclerosis. Neurology 28, 421, 1978.
21. Goust, J. M. and Fudenberg, H. H. T-cell binding to B lymphoid cell lines in humans: A marker for T-B cell interaction? J. Immunol. Meth. 59, 29, 1983.
22. Khansari, N., Petrini, M., Ambrogio, F., Goldschmidt-Clermont, P. and Fudenberg, H. H. Role of autorosette cells in antibody synthesis in vitro: Suppressive activity of ARFC in humoral immune response. Immunobiology 166, 1, 1984.
23. Khansari, N., and Fudenberg, H. H. Functional heterogeneity of human blood monocytes. Sand. J. Immunol. 19, 337 1984.
24. Vicent, J. P., Vignon, J., Kartalouski, B., and Pert, C. B. Receptor sites for phencyclidine in mammalian brain and peripheral organs. In: "PCP: Historical and Current Perspectives" (E. F. Domino, Eds.), p. 95, NPP Books, Ann Arbor, Mich., 1981.
25. Abuzzahab, F. S., Merwin, G. E., Zimmerman, R. L., and Sherman, M. C. A double-blind investigation of Piracetam (Nootropil) versus placebo in the memory of geriatric in patients. Psychopharmacol. Bull. 14, 23, 1978.

26. Cumin, R., Bandle, E. F., Gamizu, E., and Haefely, W. E. Effects of the novel compound aniracetam (Ro13-5057) upon impaired learning and memory in rodents. Psychopharmacol 78, 104, 1982.
27. Nyback, H., Axel-Wiesel, F., and Skett, P. Effects of Piracetam on brain monoamine metabolism and serum prolactin levels in the rat. Psychopharmacol. 61, 235, 1979.
28. Wurman, R. J., Magil, S. G., and Reinstein, D. K. Piracetam diminishes hippocampal acetylcholine levels in rats. Life Sci. 28, 1091, 1981.
29. Goust, J.-M., and Fudenberg, H. H. T-cell binding to B lymphoid cell lines in humans: a marker for T-B cell interaction? J. Immunol. Meth. 59, 29, 1983.
30. Fudenberg, H. H., Whitten, H. D., Galbraith, G. M. P., Goust, G. M., and Keller, R. M. "Interactive" T-cells in individuals predisposed to viral infection. Clin. Immunol. Immunopathol., submitted, 1983.
31. Cools, A. R., and Van Rossum, J. M. Excitation-mediating and inhibition-mediating dopamine receptors: a better new concept towards an understanding of electrophysiological, biochemical, pharmacological, functional and clinical data. Psychopharmacologia 45, 243, 1976.
32. Fontana, A., McAdam, K. P., Kristensen, F., and Weber E. Biological and biochemical characterization of interleukin 1-like factor from rat $C_6$ glioma cells. Eur. J. Immunol. 13, 685, 1983.
33. Green, D., Chue, B. and Gershon, R. K. and Discrimination of 2 types of suppressor T-cells by cell surface phenotype and by function: The ability to regulate the contrasuppressor circuit. J. Med. Cell. Immunol. 1, 19, 1983.
34. Schuller-Petrovic, S., Gebhart, W., Lassmann, H., Rumpold, H., and Kraft, D. A. Shared antigenic determinant between natural killer cells and nervous tissue. Nature 306, 179, 1983.
35. Hauser, S. L., Bhan, A. K., Gilles, F. H., Hoban, C. J., Reinherz, E. L., Schlossman, S. F., and Weiner, H. L. Immunohistochemical staining of human brain with monoclonal antibodies that identify lymphocytes, monocytes, and the Ia antigen. J. Neuroimmunol. 15, 197, 1983.
36. Iqbal, K., Zaidi, T., Thompson, C. H., Merz, P. A. and Wisniewski, H. M. Alzheimer paired helical filaments: Bulk isolation. Acta Neuropathol. 62, 167, 1984.
37. Bonventre, P. F., et al., J. Immunol. 118: 1827, 1977.
38. Chide, et al., Immunol. Lett. 3: 145, 1981.
39. Dimond S. J., Brouwers E. Y. M. Increase in the power of human memory in normal man through the use of drugs. Phychopharmacol 49: 307, 1976.
40. File S. E., Hyde J. R. G. Evidence that piracetam has an anxiolytic action. J Affect Dis 1: 227, 1979.
41. Fishbein, E., et al., Immunology 50: 223, 1983.
42. Giurgea C. E., Moyersoons F. E. On the pharmacology of cortical evoked potentials. Arch Int. Pharmacol 67: 78, 1972.
43. Grayson J., Dooley N. J., Koski I. R., Blease R. M. Immunoglobulin production induced in vitro by glucocorticoid hormones. J Clin Invest 68: 1539, 1981.
44. Isselbacher K. J. Increased uptake of amino acids and 2-deoxy-D-glucose by virus transformed cells in culture. Proc Nat Aci USA 69: 585, 1972.
45. Khansari N., Fudenberg H. H., Merler E. In vitro humoral immune resonse of human peripheral blood lymphocytes to tetanus toxoid Sepharose 4B. Immunobiology 64: 42, 1983.
46. Kretschmer J. H., Kretschmer C. Zur Dosis-Wirkuegs-Relation bieder Behandlung mit Piracetam. Arzneim Forsch 26: 1158, 1976.
47. Kumagai, S., et al., Human Immun. 5: 35, 1982.
48. Mindus P., Cronholm B., Lebander S. E., Schelling D. Piracetam-induced improvement of mental performance. Psychiat Scand 54: 156, 1982.
49. Mishell R. I., Dutton R. W. Immunization of dissociated spleen cell cultures from normal mice. J. Exp Med 126: 423, 1967.
50. Mizel S. B., Rosenstreich D., Oppenheim J. J. (1978) Phorbal myristic acetate stimulates LAF production by macrophage cell line $P338D_1$. Cell Immunol 40: 230, 1978.
51. Moller G. Functional T-cell subset defined by monoclonal antibodies. Immunol Rev 74: 5, 1983.
52. Philip J. R., McCormack J. G., Moore A. L., Johnson J. E. A. lymphokine resembling transfer factor that stimulates MIF production by nonsensitive lymphocytes. J Immunol 126: 1469, 1981.
53. Rossi, F., J. Reticuloendothel. Sec. 12: 127, 1972.
54. Rucheton, M., et al., Cell, Immunol. 64: 312, 1981.
55. Smith D. E., Gorski, J. Estrogen control of uterine glucose metabolism: an analysis based on transport and phosphorylation of 2-deoxyglucose. J. Biol. Chem. 243: 4169, 1968.
56. Smith. D. E., Gorski, J. Cell, Immunol. 64: 312, 1981.
57. Terry, R. D. and Davies, P. Dementia of the Alzheimer type. Ann. Rev. Neurosci. 3, 77, 1980.
58. Terry, R. D., Peck, A., Deteresa, R., Schechter, R., and Hauropian, D. S. Some morphemetric aspects of the brain in senile dementia of the Alzheimer type. Ann. 1 Neurol. 10, 184, 1981.

We claim:

1. A method of diagnosing a degenerative disease of the central nervous system associated with the impairment of integrative brain function, comprising
   (a) providing a peripheral blood sample from a patient,
   (b) measuring the level of interactive T cells of said peripheral blood, and
   (c) determining whether the patient suffers from a degenerative disease of the central nervous system associated with the impairment of integrative brain function by comparing said level with a predetermined standard level indicative of the degenerative disease or with a predetermined standard level indicative of normality.

2. The method of claim 1 in which the disease is a dementia of the Alzheimer's type.

3. A method for the in vitro testing of the efficacy of a therapeutic agent in treating a degenerative disease or condition of the central nervous system associated with the impairment of integrative brain function comprising
   (a) taking a peripheral blood sample from an individual known to be suffering from a degenerative disease or condition of the central nervous system associated with the impairment of integrative brain function,
   (b) measuring the level of interactive T cells of said sample,
   (c) exposing said sample to the action of a therapeutic agent in a predetermined dosage for a predetermined period of time, and again
   (d) measuring said level of interactive T cells, whereby a change in said level toward a predetermined standard level indicative of normality, is suggestive of efficacy of the therapeutic agent.

4. The method of claim 3, wherein the disease is one of the diseases associated with Alzheimer's syndrome.

5. A method of distinguishing Alzheimer's disease from another senile dementia, comprising
   (a) providing a peripheral blood sample from a patient,
   (b) measuring the level of interactive T cells of said peripheral blood, and
   (c) determining whether the patient suffers from Alzheimer's disease or another senile dementia by comparing said level with a predetermined standard level indicative of Alzheimer's disease and a predetermined standard level indicative of another senile dementia.

6. A method of diagnosing in a patient a disease characterized by a structural brain abnormality comprising
   (a) providing a peripheral blood sample from a patient,
   (b) measuring the level of interactive T cells of said peripheral blood, and
   (c) determining whether the patient suffers from a disease characterized by a structural brain abnormality by comparing said level with a predetermined standard level indicative of the disease or with a predetermined standard level indicative of normality.

7. The method of claim 6 in which the abnormality is atrophy of the basal nucleus of Meynert.

8. A method of diagnosing in a patient a disease characterized by reduced levels of choline acetyltransferase or acetylcholine esterase comprising
   (a) providing a peripheral blood sample from a patient,
   (b) measuring the level of interactive T cells of said peripheral blood, and
   (c) determining whether the patient suffers from a disease characterized by reduced levels of choline acetyltransferase or acetylcholine esterase by comparing the level of interactive T cells with a predetermined standard level indicative of the disease or with a predetermined standard level indicative of normality.

9. A method of diagnosing in a patient a dementing disorder comprising
   (a) providing a peripheral blood sample from a patient,
   (b) measuring the level of interactive T cells of said peripheral blood, and
   (c) determining whether the patient suffers from a dementing disorder by comparing said level with a predetermined standard level indicative of the dementing disorder or with a predetermined standard level indicative of normality.

10. A method of in vitro testing a substance for potential nootropic action comprising
    (a) providing a sample of peripheral blood immunocytes from a patient,
    (b) contacting said immunocytes with a substance with potential nootropic action,
    (c) observing the effect of said substance on the ability of said immunocytes to form rosettes with human B lymphoid cells, the level of rosettes formed being an indication of the nootropic action of said substance.

11. A method of in vitro testing a substance for potential therapeutic use against a dementing disorder comprising
    (a) providing a sample of peripheral blood immunocytes from a patient,
    (b) contacting said immunocytes with a substance with potential nootropic action,
    (c) observing the effect of said substance on the ability of said immunocytes to form rosettes with human B lymphoid cells, the level of rosettes formed being an indication of the therapeutic efficacy of said substance.

* * * * *